US012573476B2

(12) United States Patent
Rong et al.

(10) Patent No.: US 12,573,476 B2
(45) Date of Patent: Mar. 10, 2026

(54) COMPOUND PROPERTY ANALYSIS METHOD, MODEL TRAINING METHOD, APPARATUSES, AND STORAGE MEDIUM

(71) Applicant: TENCENT TECHNOLOGY (SHENZHEN) COMPANY LIMITED, Guangdong (CN)

(72) Inventors: Yu Rong, Guangdong (CN); Wenbing Huang, Guangdong (CN); Tingyang Xu, Guangdong (CN)

(73) Assignee: Tencent Technology (Shenzhen) Company Limited, Shenzhen (CN)

( * ) Notice: Subject to any disclaimer, the term of this patent is extended or adjusted under 35 U.S.C. 154(b) by 1172 days.

(21) Appl. No.: 17/452,171

(22) Filed: Oct. 25, 2021

(65) Prior Publication Data

US 2022/0044767 A1 Feb. 10, 2022

Related U.S. Application Data

(63) Continuation of application No. PCT/CN2020/115988, filed on Sep. 17, 2020.

(30) Foreign Application Priority Data

Nov. 28, 2019 (CN) .......................... 201911193424.3

(51) Int. Cl.
*G16C 20/20* (2019.01)
*G06F 18/214* (2023.01)
(Continued)

(52) U.S. Cl.
CPC ........... *G16C 20/20* (2019.02); *G06F 18/214* (2023.01); *G06F 18/241* (2023.01); *G06N 20/00* (2019.01); *G16C 20/70* (2019.02)

(58) Field of Classification Search
CPC ........ G16C 20/20; G16C 20/70; G06N 20/00; G06F 18/214; G06F 18/241
(Continued)

(56) References Cited

U.S. PATENT DOCUMENTS 8,718,375 B2 5/2014 Ouyang et al.
11,087,861 B2 * 8/2021 Takeda ................... G16C 20/20
(Continued)

FOREIGN PATENT DOCUMENTS

CN 106874688 A 6/2017
CN 107880934 A 4/2018
(Continued)

OTHER PUBLICATIONS

Olayan et al. (DDR: efficient computational method to predict drug-target interactions using graph mining and machine learning approaches, Bioinformatics, 2018, pp. 1164-1173) (Year: 2018).*
(Continued)

*Primary Examiner* — Iftekhar A Khan
(74) *Attorney, Agent, or Firm* — ArentFox Schiff LLP

(57) ABSTRACT

A compound property analysis method is provided. The method includes obtaining, according to a molecular structure of a compound, a feature vector of the compound, the feature vector including a node vector of each node and an edge vector of each edge, processing the feature vector by using a feature map extraction model branch to obtain a graph representation vector, and processing the graph representation vector by using a classification model branch to obtain a property of the compound. Thus, in the process of compound property analysis, the graph representation vector that can accurately represent a feature of the compound is obtained based on a graph data structure of the compound, and a classification property of the compound may be obtained based on the graph representation vector, thereby
(Continued)

improving the accuracy of determining the classification property of the compound. Apparatus and non-transitory computer-readable storage medium counterpart embodiments are also provided.

20 Claims, 8 Drawing Sheets

(51) Int. Cl.
    *G06F 18/241*     (2023.01)
    *G06N 20/00*     (2019.01)
    *G16C 20/70*     (2019.01)

(58) Field of Classification Search
    USPC .......................................................... 703/2
    See application file for complete search history.

(56)               References Cited

U.S. PATENT DOCUMENTS

| | | | |
|---|---|---|---|
| 11,450,410 | B2 * | 9/2022 | Yoo ....................... G06N 3/0499 |
| 11,636,920 | B2 * | 4/2023 | Xiong .................... G16B 20/00 |
| | | | 703/11 |
| 11,727,282 | B2 * | 8/2023 | Feinberg ............... G16C 20/70 |
| | | | 706/21 |
| 11,854,671 | B2 * | 12/2023 | Rong ..................... G16C 20/30 |
| 2001/0044699 | A1 * | 11/2001 | Ewing ................... G16B 15/00 |
| | | | 702/19 |
| 2002/0029114 | A1 * | 3/2002 | Lobanov ............... G06N 20/00 |
| | | | 702/22 |
| 2019/0080057 | A1 * | 3/2019 | Stanley .................. G06V 10/82 |
| 2019/0272468 | A1 * | 9/2019 | Feinberg ............. G06N 3/0464 |
| 2019/0304568 | A1 * | 10/2019 | Wei ........................ G16B 10/00 |
| 2019/0355444 | A1 | 11/2019 | Yoo et al. |
| 2020/0294630 | A1 * | 9/2020 | Miller .................... G16C 20/10 |
| 2020/0342953 | A1 * | 10/2020 | Morrone ............. G06N 3/0464 |
| 2020/0365270 | A1 * | 11/2020 | Kazemi Oskooei ..... G06N 3/09 |
| 2021/0065913 | A1 * | 3/2021 | Yuan ........................ G06N 3/08 |
| 2021/0081717 | A1 * | 3/2021 | Creed ..................... G06N 5/02 |
| 2021/0158904 | A1 * | 5/2021 | Rong ..................... G16C 20/50 |
| 2022/0165364 | A1 * | 5/2022 | Qiao ....................... G06N 3/096 |

FOREIGN PATENT DOCUMENTS

| | | |
|---|---|---|
| CN | 108062551 A | 5/2018 |
| CN | 108520275 A | 9/2018 |
| CN | 109033738 A | 12/2018 |
| CN | 109461475 A | 3/2019 |
| CN | 110263780 A | 9/2019 |
| CN | 110767271 A | 2/2020 |
| CN | 110957012 A | 4/2020 |

OTHER PUBLICATIONS

Gilmer et al.(Neural Message Passing for Quantum Chemistry, arXiv, 2017, pp. 1-14). (Year: 2017).*
Fei et al. ("Structure Feature Selection for Chemical Compound Classification", IEEE, 2008, pp. 1-6) (Year: 2008).*
Office Action dated Aug. 19, 2020 issued in corresponding Chinese patent application No. 201911193424.3 (with English translation) (13 pages).
Office Action dated Oct. 13, 2020 issued in corresponding Chinese patent application No. 201911193424.3 (with English translation) (9 pages).
Supplementary European Search Report issued Feb. 22, 2023 in Application No. 20894594.9, pp. 1-8.
Kevin Yang et al: "Analyzing Learned Molecular Representations for Property Prediction", arxiv.org, Cornell University Library, 201 Olin Library Cornell University Ithaca, NY 14853, Nov. 20, 2019.
Peter Cst John et al: "Message-passing neural networks for high-throughput polymer screening", arxiv.org, Cornell University Library, 201 Olin Library Cornell University Ithaca, NY 14853, Apr. 5, 2019.
Peter Bjorn Jorgensen et al: "Neural Message Passing with Edge Updates for Predicting Properties of Molecules and Materials" arxiv.org, Cornell University Library, 201 Olin Library Cornell University Ithaca, NY 14853, Jun. 8, 2018.
Gilmer et al.—Neural Message Passing for Quantum Chemistry [Online]) (non-official translation: From the Internet <URL:) (non-official translation: Search From https://arxiv.orglpdj/1704.01212. pdf> ), Jun. 12, 2017, (10 pages).
Written Opinion dated Dec. 16, 2020 issued in corresponding patent application No. PCT/CN2020/115988 (5 pages).
International Search Report mailed Dec. 16, 2020 issued in corresponding patent application No. PCT/CN2020/115988 (6 pages).

* cited by examiner

301
Obtain, according to a molecular structure of a compound sample, a feature vector sample of the compound sample 302
Process the feature vector sample by using a feature map extraction model branch, to obtain a graph representation vector sample outputted by the feature map extraction model branch 303
Process the graph representation vector sample by using a classification model branch to obtain a classification property of the compound sample outputted by the classification model branch 304
Adjust parameters in the feature map extraction model branch and the classification model branch according to a property of the compound sample and the classification property of the compound sample to obtain a compound analysis model including the feature map extraction model branch and the classification model branch

FIG. 3

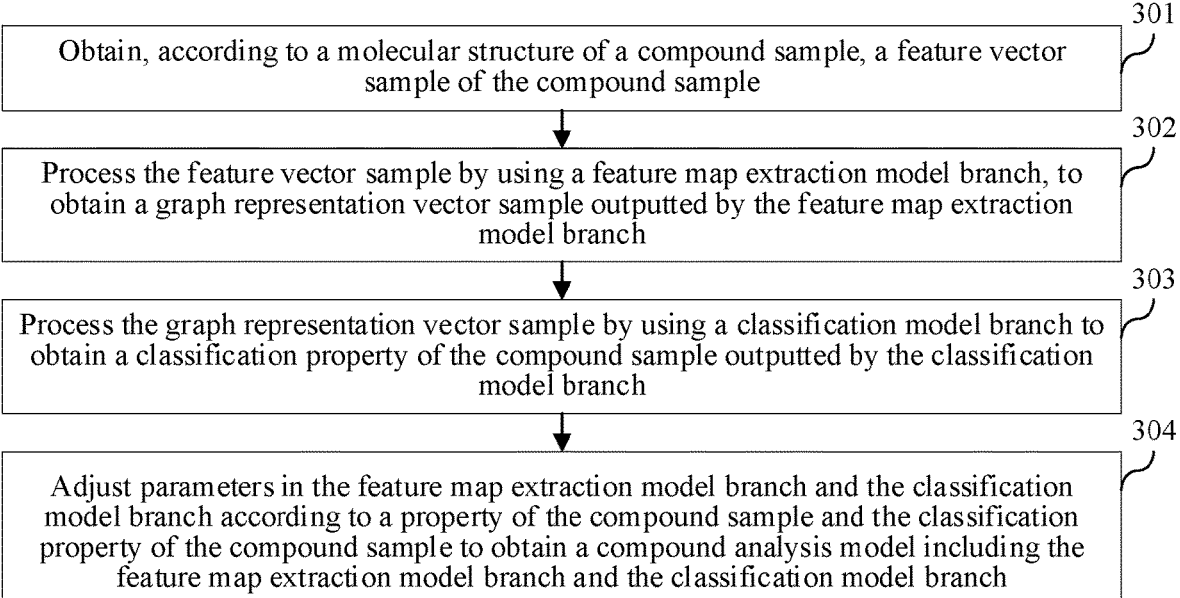

FIG. 4

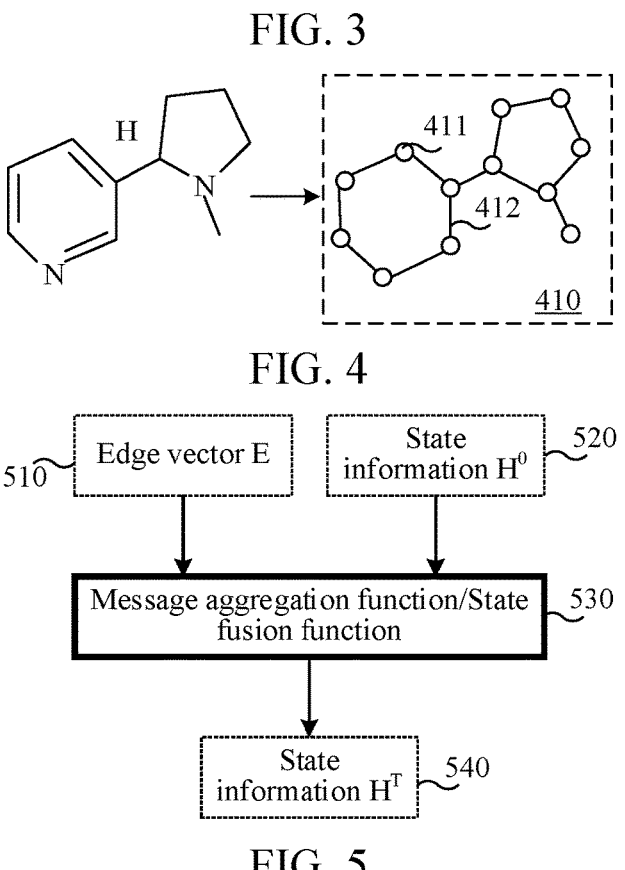

FIG. 5

COMPOUND PROPERTY ANALYSIS METHOD, MODEL TRAINING METHOD, APPARATUSES, AND STORAGE MEDIUM

RELATED APPLICATIONS

This application is a continuation of International Application No. PCT/CN2020/115988, entitled "COMPOUND PROPERTY ANALYSIS METHOD, MODEL TRAINING METHOD, APPARATUSES, AND STORAGE MEDIUM," filed Sep. 17, 2020, which claims priority to Chinese Patent Application No. 201911193424.3, entitled "COMPOUND PROPERTY ANALYSIS METHOD AND APPARATUS, DEVICE, AND STORAGE MEDIUM" and filed on Nov. 28, 2019. The entire disclosures of the above-identified prior applications are incorporated herein by reference in their entirety.

FIELD OF THE TECHNOLOGY

This application relates to the field of machine learning technologies, including a compound property analysis method, a model training method, apparatuses, and a storage medium.

BACKGROUND OF THE DISCLOSURE

In the pharmaceutical analysis, how to determine, according to the structure of a compound/protein, some chemical/biological properties, such as toxicity, solubility, and carcinogenicity, of the compound/protein is a very important task.

In the related art, this task can be modeled as a classification problem in machine learning. For example, a structural formula of a compound/protein can be converted into a vector in Euclidean space in a manner of representation learning, and then the vector is classified by using a classic machine learning algorithm, to determine chemical/biological properties of the compound/protein.

However, classification models in the related art, for example, a convolutional neural network (CNN) model, have one thing in common on source data used, that is, they have a grid structure, which cannot achieve a good classification effect for feature data of compounds that does not have the grid structure.

SUMMARY

Embodiments of this disclosure provide a compound property analysis method, a model training method, apparatuses, and a storage medium, which can improve the accuracy of compound property analysis. The technical solutions are as follows.

According to an aspect, a compound property analysis method is provided, performed by a computer device, the method including: (1) obtaining, according to a molecular structure of a compound, a feature vector of the compound, the feature vector including a node vector of each node and an edge vector of each edge, the nodes respectively corresponding to atoms in the molecular structure, and the edges respectively corresponding to chemical bonds in the molecular structure; (2) processing the feature vector by using a feature map extraction model branch in a compound property analysis model, to obtain a graph representation vector outputted by the feature map extraction model branch; and (3) processing the graph representation vector by using a classification model branch in the compound property analysis model, to obtain a property of the compound outputted by the classification model branch, the compound property analysis model being a machine learning (ML) model trained according to a molecular structure of a compound sample and a property of the compound sample.

According to another aspect, a model training method is provided, performed by a computer device, the method including: (1) obtaining, according to a molecular structure of a compound sample, a feature vector sample of the compound sample, the feature vector sample including a node vector of each node and an edge vector of each edge, the nodes respectively corresponding to atoms in the molecular structure, and the edges respectively corresponding to chemical bonds in the molecular structure; (2) processing the feature vector sample by using a feature map extraction model branch in a compound property analysis model, to obtain a graph representation vector sample outputted by the feature map extraction model branch; (3) processing the graph representation vector sample by using a classification model branch in the compound property analysis model, to obtain a classification property of the compound sample outputted by the classification model branch; and (4) adjusting parameters in the feature map extraction model branch and the classification model branch according to a property of the compound sample and the classification property of the compound sample.

According to another aspect, a compound property analysis apparatus is provided, applicable to a computer device, the apparatus including: circuitry configured to (1) obtain, according to a molecular structure of a compound, a feature vector of the compound, the feature vector including a node vector of each node and an edge vector of each edge, the nodes respectively corresponding to atoms in the molecular structure, and the edges respectively corresponding to chemical bonds in the molecular structure; (2) process the feature vector by using a feature map extraction model branch in a compound property analysis model, to obtain a graph representation vector outputted by the feature map extraction model branch; and (3) process the graph representation vector by using a classification model branch in the compound property analysis model, to obtain a property of the compound outputted by the classification model branch, the compound property analysis model being a machine learning (ML) model trained according to a molecular structure of a compound sample and a property of the compound sample.

In one implementation, the circuitry is further configured to: (1) perform, through n message passing layers in the feature map extraction model branch, n layers of message passing on state information of each node according to the edge vector of each edge, n being an integer greater than or equal to two; and (2) convert a result of an $n^{th}$ message passing layer into the graph representation vector with a fixed length by using a conversion function in the feature map extraction model branch.

In one implementation, the message passing sub-module is configured to, for an $i^{th}$ layer in the n message passing layers, (1) when i=1, process, through a first message passing layer in the feature map extraction model branch, initial state information of each node according to the edge vector of each edge, to obtain the state information corresponding to each node outputted from the first message passing layer; and (2) when $2 \le i \le n$, processing, through an $i^{th}$ message passing layer in the feature map extraction model branch, state information corresponding to each node outputted from an $(i-1)^{th}$ message passing layer according to the edge vector of each edge, to obtain the state information corresponding to each node outputted from the $i^{th}$ message passing layer.

In one implementation, the message passing layer is configured to implement passing of message information and the state information of each node by using a message aggregation function and a state fusion function; the message information of a first node at a moment t+1 is obtained by processing the state information of the first node at a moment t, the state information of a second node at the moment t, and an edge between the first node and the second node by using the message aggregation function, wherein the first node is one of the nodes, the second node is a neighbor node of the first node, and t is a natural number, and the state information of the first node at the moment t+1 is obtained by processing the state information of the first node at the moment t and the message information of the first node at the moment t+1 by using the state fusion function.

In one implementation, the circuitry is further configured to process the result of the $n^{th}$ message passing layer by using a sum function in the feature map extraction model branch, to obtain the graph representation vector with the fixed length.

In one implementation, the circuitry is further configured to: (1) obtain a specified property type before the processing the feature vector by using a feature map extraction model branch in a compound property analysis model, to obtain a graph representation vector outputted by the feature map extraction model branch; and (2) determine the corresponding compound property analysis model according to the property type.

In one implementation, the property type obtained by the circuitry includes at least one of a chemical property, a physical property, and a biological property.

According to another aspect, a model training apparatus is provided, the apparatus including: circuitry configured to (1) obtain, according to a molecular structure of a compound sample, a feature vector sample of the compound sample, the feature vector sample including a node vector of each node and an edge vector of each edge, the nodes respectively corresponding to atoms in the molecular structure, and the edges respectively corresponding to chemical bonds in the molecular structure; (2) process the feature vector sample by using a feature map extraction model branch in a compound property analysis model, to obtain a graph representation vector sample outputted by the feature map extraction model branch; (3) process the graph representation vector sample by using a classification model branch in the compound property analysis model, to obtain a classification property of the compound sample outputted by the classification model branch; and (4) adjust parameters in the feature map extraction model branch and the classification model branch according to a property of the compound sample and the classification property of the compound sample.

In one implementation, the circuitry is further configured to: (1) input the property of the compound sample and the classification property of the compound sample to a loss function to obtain a loss function value; and (2) adjust the parameters in the feature map extraction model branch and the classification model branch according to the loss function value.

In one implementation, the circuitry is further configured to adjust, in response to the loss function value being greater than a preset threshold, the parameters in the feature map extraction model branch and the classification model branch according to the loss function value.

According to another aspect, a computer device is provided, including a processor (processing circuitry) and a memory, the memory storing at least one instruction, at least one program, a code set, or an instruction set, the at least one instruction, the at least one program, the code set, or the instruction set being loaded and executed by the processor (processing circuitry) to implement the foregoing compound property analysis method, or the at least one instruction, the at least one program, the code set, or the instruction set being loaded and executed by the processor to implement the foregoing model training method.

According to another aspect, a non-transitory computer-readable storage medium is provided, the storage medium storing at least one instruction, at least one program, a code set, or an instruction set, the at least one instruction, the at least one program, the code set, or the instruction set being loaded and executed by a processor (processing circuitry) to implement the foregoing compound property analysis method, or the at least one instruction, the at least one program, the code set, or the instruction set being loaded and executed by a processor (processing circuitry) to implement the foregoing model training method.

According to another aspect, a computer program product or a computer program is provided, the computer program product or the computer program including computer instructions, the computer instructions being stored in a computer-readable storage medium. A processor (processing circuitry) of a computer device reads the computer instructions from the computer-readable storage medium, and executes the computer instructions, so that the computer device performs the compound property analysis method or the model training method in the foregoing implementations.

The technical solutions provided in this disclosure may include the following beneficial effects.

A feature vector of a compound is obtained according to a molecular structure of the compound; the feature vector is processed by using a feature map extraction model branch to obtain a graph representation vector; and the graph representation vector is processed by using a classification model branch to obtain a property of the compound. In this case, in the process of compound property analysis, the graph representation vector that can accurately represent a feature of the compound can be obtained based on a graph data structure of the compound, and a classification property of the compound can be obtained based on the graph representation vector, thereby improving the accuracy of determining the classification property of the compound.

It is to be understood that the foregoing general descriptions and the following detailed descriptions are merely exemplary and explanatory, and are not intended to limit this disclosure.

BRIEF DESCRIPTION OF THE DRAWINGS

Accompanying drawings herein are incorporated into this specification and constitute a part of this specification, show embodiments that conform to this disclosure, and are used for describing a principle of this disclosure together with this specification.

FIG. 3 is a schematic flowchart of a model training method according to an exemplary embodiment of this disclosure.

FIG. 4 is a schematic diagram of a data structure of a nicotine branch according to an exemplary embodiment of this disclosure.

FIG. 5 is a schematic diagram of input and output of a message passing layer according to an exemplary embodiment of this disclosure.

DESCRIPTION OF EMBODIMENTS

Figures 1, 2:
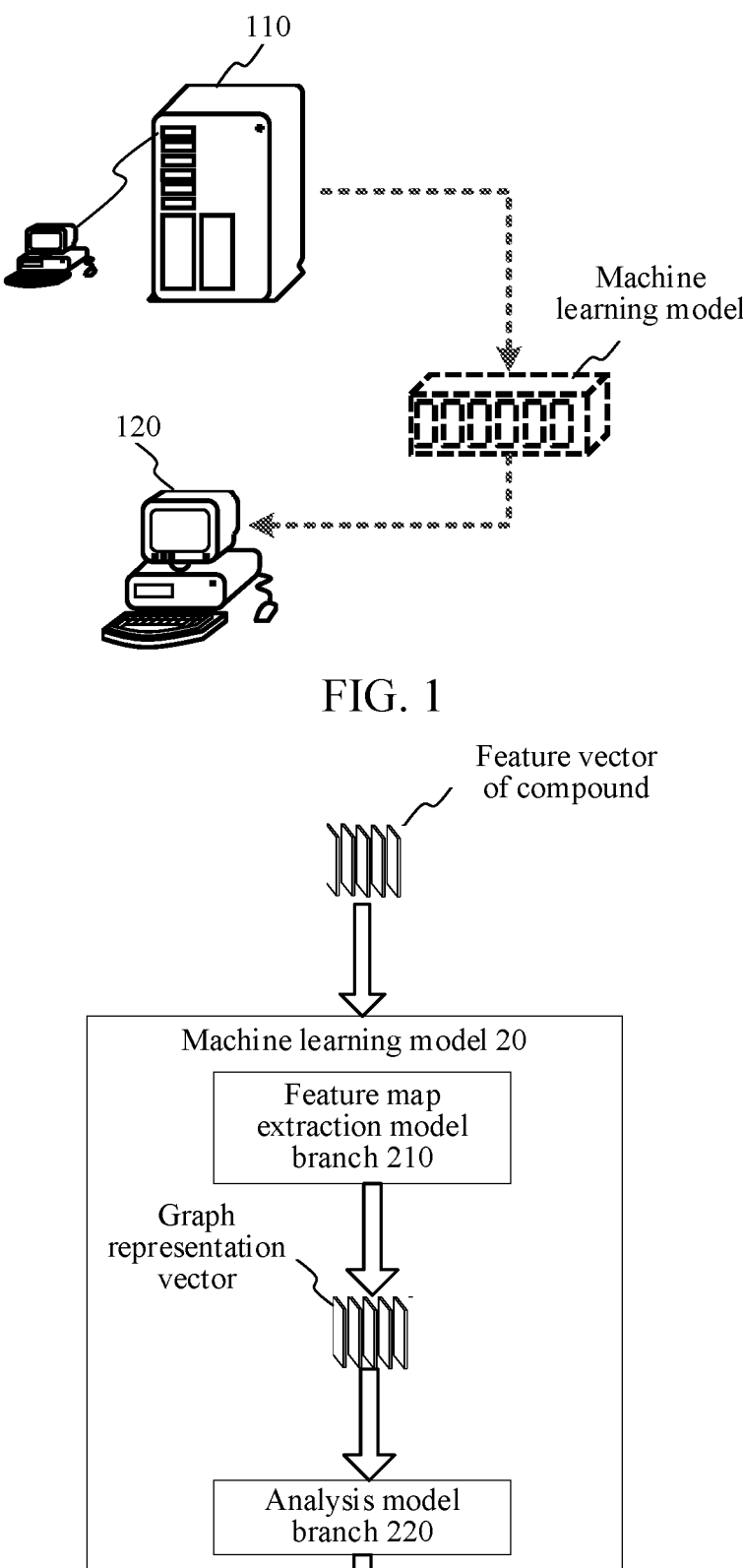
FIG. 1 is a framework diagram of model training and compound property analysis according to an exemplary embodiment.
FIG. 2 is a model architecture diagram of a machine learning model according to an exemplary embodiment.

Exemplary embodiments are described in detail herein, and examples of the exemplary embodiments are shown in the accompanying drawings. When the following description involves the accompanying drawings, unless otherwise indicated, the same numerals in different accompanying drawings represent the same or similar elements. The implementations described in the following exemplary embodiments do not represent all implementations that are consistent with this disclosure. On the contrary, the implementations are merely examples of apparatuses and methods that are described in detail in the appended claims and that are consistent with some aspects of this disclosure.

It is to be understood that, in this specification, "several" refers to one or more, and "plurality of" refers to two or more. "And/or" describes an association relationship between associated objects and represents that three relationships may exist. For example, A and/or B may represent the following three cases: only A exists, both A and B exist, and only B exists. The character "/" in this specification generally indicates an "or" relationship between the associated objects.

This disclosure provides a compound property analysis method, which can accurately recognize chemical/biological properties of compounds by a machine learning (ML) method, so as to achieve property analysis of compounds with unknown properties based on artificial intelligence (AI). For ease of understanding, several terms involved in this disclosure are explained below.

(1) Compound

A compound may be a pure substance composed of two or more different elements (different from an elementary substance). Regardless of the source, a compound has a certain composition. Compounds may be classified into organic compounds and inorganic compounds according to the composition, or may be classified into ionic compounds, covalent compounds, coordination complexes according to the chemical bond. Each compound has its own properties (or referred to as characteristics).

(2) Properties of the Compound

The properties of the compound in this disclosure may be classified into chemical properties, biological properties, physical properties, and the like.

The chemical properties refer to properties of substances (for example, compounds) in chemical changes, such as combustibility, stability, instability, thermostability, acidity, alkalinity, oxidation, combustion-supporting, reduction, complexity, toxicity, corrosiveness, metallicity, and non-metallicity.

The biological properties may include biological activity (or immunity) and the like.

The physical properties refer to properties of substances that do not need to undergo chemical changes, such as color, smell, state, easy melting, easy solidification, easy sublimability, volatility, melting point, boiling point, hardness, electrical conductivity, thermal conductivity, and ductility.

(3) AI

AI is a theory, method, technology, and application system that uses a digital computer or a machine controlled by the digital computer to simulate, extend, and expand human intelligence, perceive an environment, acquire knowledge, and use knowledge to obtain an optimal result. In other words, AI is a comprehensive technology of the computer sciences, attempts to understand the essence of intelligence, and produces a new intelligent machine that can react in a manner similar to human intelligence. AI governs the design principles and implementation methods of various intelligent machines, so that the machines can perceive, infer, and make decisions.

AI technology is a comprehensive discipline and relates to a wide range of fields including both hardware-level technologies and software-level technologies. Basic AI technologies generally include technologies such as a sensor, a dedicated AI chip, cloud computing, distributed storage, a big data processing technology, an operating/interaction system, and electromechanical integration. AI software technologies mainly include several major technologies such as a computer vision (CV) technology, a speech processing technology, natural language processing technology, and ML/deep learning.

(4) ML

ML is a multi-field interdisciplinary subject involving probability theory, statistics, approximation theory, convex analysis, algorithm complexity theory, and the like. ML specializes in studying how a computer simulates or implements a human learning behavior to obtain new knowledge or skills, and reorganize an existing knowledge structure, so as to keep improving its performance. ML is the core of AI, is a basic way to make the computer intelligent, and is applied to various fields of AI. ML and deep learning generally include technologies such as artificial neural networks, belief networks, reinforcement learning, transfer learning, inductive learning, and learning from demonstrations.

With the research and progress of AI technology, AI technology is studied and applied in a plurality of fields such as a common smart home, a smart wearable device, a virtual assistant, a smart speaker, smart marketing, unmanned driving, automatic driving, an unmanned aerial vehicle, a robot, smart medical care, and smart customer service. It is believed that with the development of technologies, AI technology will be applied to more fields, and play an increasingly important role.

Solutions provided in the embodiments of this disclosure involve technologies such as ML of AI, that is, automatic analysis and prediction of compound properties is achieved through ML.

The solutions of the embodiments of this disclosure include a model training stage and an analysis stage. FIG. 1 is a framework diagram of model training and compound property analysis according to an exemplary embodiment. As shown in FIG. 1, in the model training stage, a model training device 110 trains an end-to-end ML model based on a molecular structure of a compound sample and a pre-marked property of the compound sample, and in the property analysis stage, an analysis device 120 directly analyzes a property of a compound according to the trained ML model and an inputted molecular structure of the compound.

The model training device 110 and the analysis device 120 may be computer devices with an ML capability. For example, the computer device may be a fixed computer device such as a personal computer, a server, or a fixed medical device; alternatively, the computer device may be a mobile computer device such as a tablet computer, an e-book reader, or a portable medical device.

The model training device 110 and the analysis device 120 may be the same device; alternatively, the model training device 110 and the analysis device 120 may be different devices. Moreover, when the model training device 110 and the analysis device 120 are different devices, the model training device 110 and the analysis device 120 may be devices of the same type, for example, the model training device 110 and the analysis device 120 may both be personal computers; alternatively, the model training device 110 and the analysis device 120 may be devices of different types, for example, the model training device 110 may be a server, and the analysis device 120 may be a portable medical device that provides compound property analysis services. Specific types of the model training device 110 and the analysis device 120 are not limited in the embodiments of this disclosure.

FIG. 2 is a model architecture diagram of a machine learning model according to an exemplary embodiment. As shown in FIG. 2, in this embodiment of this disclosure, an ML model 20 (that is, a compound property analysis model) may be configured in the analysis device 120 in FIG. 1. The ML model 20 includes two model branches (processing modules). The analysis device 120 first obtains a feature vector of a compound according to a molecular structure of the compound, and the feature vector may be in the form of a graph. A feature map extraction model branch 210 is configured to extract a graph representation vector according to the inputted feature vector of the compound and input the graph representation vector to an analysis model branch 220. The analysis model branch 220 is configured to perform ML analysis according to the graph representation vector input-ted from the feature map extraction model branch 210 and output an analysis and prediction result including a property of the compound.

Feature data of compounds does not have a grid structure. Therefore, in the foregoing ML model shown in FIG. 2 of this disclosure, convolution processing is not directly per-formed on the feature data of a compound by using a CNN, but graph feature extraction is performed on a feature vector of the compound by using the feature map extraction model branch 210, to obtain the graph representation vector, and then ML prediction is performed on the graph representation vector by using the analysis model branch to obtain the property of the compound, so that the prediction of the property of the compound is achieved based on a new method of modeling the compound, and the accuracy of compound property analysis can be improved.

An application manner of this disclosure on a product side is backend recognition. For example, for compounds that are newly discovered or synthesized in the laboratory, or for compounds that are currently less recognized, analysts can input a molecular structure of a compound to an analysis device, and the analysis device performs prediction and analysis by using a compound property analysis model, to obtain a predicted property of the compound.

The foregoing analysis device may be implemented as a server that provides external compound analysis service interfaces, and analysts call a compound analysis service interface by using a terminal device, for example, a personal computer, to input the molecular structure of the compound to the analysis device. Alternatively, the foregoing analysis device may be an offline device, and analysts may input the molecular structure of the compound in a graphical interface provided by the analysis device. A type of the analysis device is not limited in this disclosure.

FIG. 3 is a schematic flowchart of a model training method according to an exemplary embodiment of this disclosure. The model training method may be applied to a computer device (processing circuitry), for example, to the model training device 110 shown in FIG. 1, to obtain the ML model shown in FIG. 2 through training. As shown in FIG. 3, the model training method may include the following steps.

In Step 301, according to a molecular structure of a compound sample, a feature vector sample of the compound sample is obtained.

The feature vector sample refers to a feature vector of the compound sample.

In this embodiment, the feature vector includes a node vector of each node and an edge vector of each edge. The nodes are respectively corresponding to atoms in the molecular structure of the compound (for example, the compound sample), and the edges are respectively corre-sponding to chemical bonds in the molecular structure of the compound.

The compound is composed of atoms of a plurality of different elements, and the atoms in the compound are held together by chemical bonds. Therefore, the molecular struc-ture of the compound can be regarded as an undirected network graph with atoms as nodes and chemical bonds as edges. Based on the special form of the molecular structure of the compound, this embodiment may define the feature vector in the form of a graph for the molecular structure of the compound.

For example, this embodiment defines the feature vector in the form of the graph: $G(V,E)$, where V is a node set, and E is an edge set. Both the nodes and edges of the graph may have their own feature vectors. For example, $x_v$ may repre-sent the feature vector of a node v, and $e_{vw}$ may represent the feature vector of an edge vw between a node v and a node w. Such a data structure may conveniently represent a chemical molecule of the compound.

For example, FIG. 4 is a schematic diagram of a data structure of a nicotine branch according to an exemplary embodiment of this disclosure. As shown in FIG. 4, a nicotine molecule (with a chemical formula of $C_{10}H_4N_2$) may be represented as the data structure as a graph 410, where atoms are nodes 411 on the graph 410, and chemical bonds are edges 412 on the graph 410. Attributes of the atoms, such as a charge number, a proton number, and a neutron number, may be modeled as feature vectors (that is, the node vectors V) of the atoms. Attributes of the chemical bonds, such as a chemical bond type and a chemical bond valence, may be modeled as feature vectors (that is, the edge vectors E) of the edges. In this case, the chemical molecule can be modeled as a graph G. Properties (such as water solubility and toxicity) expected to be predicted in this disclosure are some labels (marked as $y_i$). An objective of this disclosure is to obtain a model M by training based on a set of given chemical molecular data $\{G_i y_i\}_{i=1}^m$, with a known property, and input a molecular structure of any compound with an unknown property into the model M, so as to predict the property of the compound.

In Step 302, the feature vector sample is processed by using a feature map extraction model branch, to obtain a graph representation vector sample outputted by the feature map extraction model branch.

In this embodiment, the compound property may be modeled by using a representation learning model based on a plurality of layers of message passing, so as to achieve the purpose of determining a corresponding property of any inputted compound.

For example, the foregoing feature map extraction model branch includes n message passing layers (n is an integer greater than or equal to 2) and a conversion function. The n message passing layers are used to perform feature extraction based on the plurality of layers of message passing to obtain a feature extraction result. The conversion function is used to normalize the feature extraction result.

That is, in this embodiment, when the feature vector sample is processed by using the feature map extraction model branch to obtain the graph representation vector sample outputted by the feature map extraction model branch, a computer device may perform, through the n message passing layers in the feature map extraction model branch, n layers of message passing on state information of each node in the feature vector sample according to the edge vector of each edge in the feature vector sample, and then convert the feature extraction result of an $n^{th}$ message passing layer into the graph representation vector with a fixed length by using the conversion function in the feature map extraction model branch.

In this embodiment, the foregoing feature map extraction model branch may be a multi-layer node information propagation model based on edge sharing. That is, when the n message passing layers perform message passing on the inputted state information of each node, the edge vector in the feature vector sample may be shared to achieve combined extraction of features of the node vector and edge vector in the feature vector sample, so that the finally extracted graph representation vector includes both the feature of the node vector and the feature of the edge vector.

For example, when the n layers of message passing is performed, through the n message passing layers in the feature map extraction model branch, on the state information of each node in the feature vector sample according to the edge vector of each edge in the feature vector sample, for an $i^{th}$ layer in the n message passing layers, When i=1, the computer device may process, through a first message passing layer in the feature map extraction model branch, initial state information of each node in the feature vector sample according to the edge vector of each edge in the feature vector sample, to obtain state information corresponding to each node in the feature vector sample outputted from the first message passing layer; and When 2≤i≤n, the computer device may process, through an $i^{th}$ message passing layer in the feature map extraction model branch, state information corresponding to each node in the feature vector sample outputted from an $(i-1)^{th}$ message passing layer according to the edge vector of each edge in the feature vector sample, to obtain state information corresponding to each node in the feature vector sample outputted from the $i^{th}$ message passing layer.

In this embodiment, a developer may pre-design the foregoing message passing layers, so that each message passing layer can share the edge vector of each edge. In addition, the state information of each node is passed using an output of a previous layer as an input of a current layer, and the feature extraction in the form of the graph is performed while passing the state information.

In one implementation, the message passing layer is configured to implement passing of message information and state information of each node by using a message aggregation function and a state fusion function; and the performing, through n message passing layers in the feature map extraction model branch, n layers of message passing on state information of each node according to the edge vector of each edge includes: (1) processing the state information of a first node at a moment t, the state information of a second node at the moment t, and an edge between the first node and the second node by using the message aggregation function to obtain the message information of the first node at a moment t+1, the first node being any one of the nodes, and the second node being a neighbor node of the first node, t being a natural number; and (2) processing the state information of the first node at the moment t and the message information of the first node at the moment t+1 by using the state fusion function to obtain the state information of the first node at the moment t+1.

For example, if the first node is a node v, and the second node is a node w, the message information of the node v at the moment t+1 is obtained by processing the state information of the node v at the moment t, the state information of the node w at the moment t, and the edge between node v and the node w by using the message aggregation function, the node v being any one of the nodes, and the node w being a neighbor node of the node v; and the state information of the node v at the moment t+1 is obtained by processing the state information of the node v at the moment t and the message information of the node v at the moment t+1 by using the state fusion function.

Here, t is an integer greater than or equal to 0, and the moment t+1 refers to a moment of passing the message information and the state information of each node by a $(t+1)^{th}$ message passing layer in the message passing layers. When t=0, the state information of each node is initial state information of each node.

In this embodiment, the message passing layers may pass the message information and the state information of each node according to the message information and the state information of each node combining with the shared edge vectors between the nodes. In each message passing layer, the message information and the state information of each node are determined by the inputted state information of the node, the inputted state information of an adjacent node of the node, and the edge vector between the node and the adjacent node.

In one implementation, the conversion function is a sum function; and when a result of the $n^{th}$ message passing layer is converted into the graph representation vector with a fixed length by using the conversion function in the feature map extraction model branch, the computer device may process the result of the $n^{th}$ message passing layer by using the sum function to obtain the graph representation vector with a fixed length.

For example, in one implementation, the model M may convert a molecular structure of any compound into a vector g with a fixed length, and then process the vector g by using a classification/regression device to predict the property of the compound.

In addition to the sum function, the conversion function may alternatively be implemented as a function of other types. For example, the conversion function may be implemented as a max pooling layer, that is, taking a maximum value in a sliding window with a fixed size, or may be implemented as a function based on a self-attention mechanism.

In Step 303, the graph representation vector sample is processed by using a classification model branch to obtain a classification property of the compound sample outputted by the classification model branch.

The classification model branch may be an ML model used for classification/regression, such as a logistic regression model, a decision tree model, a random forest model, a gradient boosting tree model, a multilayer perceptron model, a support vector machine model, and a naive Bayes model. The ML model may output the property of the corresponding compound according to the inputted graph representation vector.

In Step 304, parameters in the feature map extraction model branch and the classification model branch are adjusted according to a property of the compound sample and the classification property of the compound sample to obtain a compound analysis model including the feature map extraction model branch and the classification model branch.

In this embodiment, in the process of training the feature map extraction model branch and the classification model branch, the parameters in the feature map extraction model branch and the classification model branch may be adjusted according to a difference between the predicted classification property of the compound sample and the actual property of the compound sample until a training result converges, so that the compound analysis model including the feature map extraction model branch and the classification model branch can be obtained.

In one implementation, when the parameters in the feature map extraction model branch and the classification model branch are adjusted according to the property of the compound sample and the classification property of the compound sample, the computer device (processing circuitry) may input the property of the compound sample and the classification property of the compound sample to a loss function to obtain a loss function value, and then update the parameters in the feature map extraction model branch and the classification model branch according to the loss function value.

In this embodiment, in the process of training, the computer device may calculate the loss function value according to the predicted classification property of the compound sample and the actual property of the compound sample, and update the parameters in the feature map extraction model branch and the classification model branch according to the loss function value.

When the loss function value is greater than a preset threshold, the computer device may perform the step of updating the parameters in the feature map extraction model branch and the classification model branch according to the loss function value.

In this embodiment, after obtaining the loss function value, the computer device may determine whether the model training converges according to the loss function value, for example, determining whether the loss function value is greater than the preset threshold. If the loss function value is greater than the preset threshold, it indicates that the model training does not converge, and the step of updating the parameters in the feature map extraction model branch and the classification model branch according to the loss function value can be performed; otherwise, it can be considered that the model training converges, and the trained model parameters can be outputted.

In addition to comparing the loss function value with the preset threshold, the computer device may alternatively determine whether the model training converges in other ways. For example, whether the model training converges is determined according to a variance of the loss function value obtained through multiple iterations. When the variance of the loss function value is less than a certain variance threshold, it is determined that the model training converges, otherwise, it is considered that the model training does not converge. In another example, the accuracy of a model obtained after each iteration is verified according to a verification dataset. When the accuracy reaches a preset accuracy threshold, it is determined that the model training converges, otherwise, it is considered that the model training does not converge; alternatively, when a variance of the accuracy of a model after multiple iterations is less than a certain variance threshold, it is determined that the model training converges, otherwise, it is considered that the model training does not converge.

In this embodiment, message propagation on a graph may be defined as follows.

First, a process of message propagation based on a node v may be defined as follows:

$$m_v^{t+1} = \sum_{w \in N(v)} K_i(h_v^t, h_w^t, e_{vw}) \tag{1}$$

$$h_v^{t+1} = S_i(h_v^t, m_v^{t+1}) \tag{2}$$

In the foregoing two formulas, $m_v^t$ represents message information of the node v at a moment t, $h_v^t$ represents state information of the node at the moment t, $N(v)$ represents a neighbor set of the node v, $K_i(.)$ represents a message aggregation function, and $S_i(.)$ represents a state fusion function.

In this embodiment of this disclosure, $K_i$ may be defined as:

$$K_i(h_v, h_w, e_{vw}) = \sigma(W_K \text{concat}(h_w, e_{vw}))$$

wherein $\sigma(.)$ represents an activation function. The activation function may be ReLu(x)=max(0, x), $$\text{Sigmoid}(x) = \frac{1}{1 + e^{-x}},$$

or the like, and a concat function is a concatenation function, that is, concatenating two vectors together.

$$W_K \in R^{d_m \times d_{h_w} + d_{e_{vw}}}$$

is a parameter of the message aggregation function.

Similarly, $S_i$ is defined as:

$$S_i(h_v^t, m_v^{t+1}) = \sigma(h_v^0 + W_S m_v^{t+1})$$

$h_v^0$ is input state information of the node v, which is defined as: $h_v^0 = \sigma(W_{in} x_v)$, $$W_{in} \in R^{d_{h_v}^0 \times d_x}$$

is an input parameter, and $$W_S \in R^{d_{h_v}^0 \times d_{m_v}^{t+1}}$$

is a fusion function parameter.

Through the foregoing propagation process, a new feature $h_v^T$ of node features can be obtained, and T is a number of times of message propagation. Herein, $W_K$ and $W_S$ can be shared in propagation process.

FIG. 5 is a schematic diagram of input and output of a message passing layer according to an exemplary embodiment of this disclosure. As shown in FIG. 5, $H^0 = \{h_v^0\}_{v \in V}$ is a set representation of an input state vector of each node, $H^T = \{h_v^T\}_{v \in V}$ is a set representation of an output state vector of each node, and E is a set representation of an edge vector of each node. After an edge vector set 510 and an input state vector set 520 are inputted to and processed by a message passing layer 530, an output state vector 540 is obtained. The message passing layer 530 includes a message aggregation function and a state fusion function.

Figure 6:
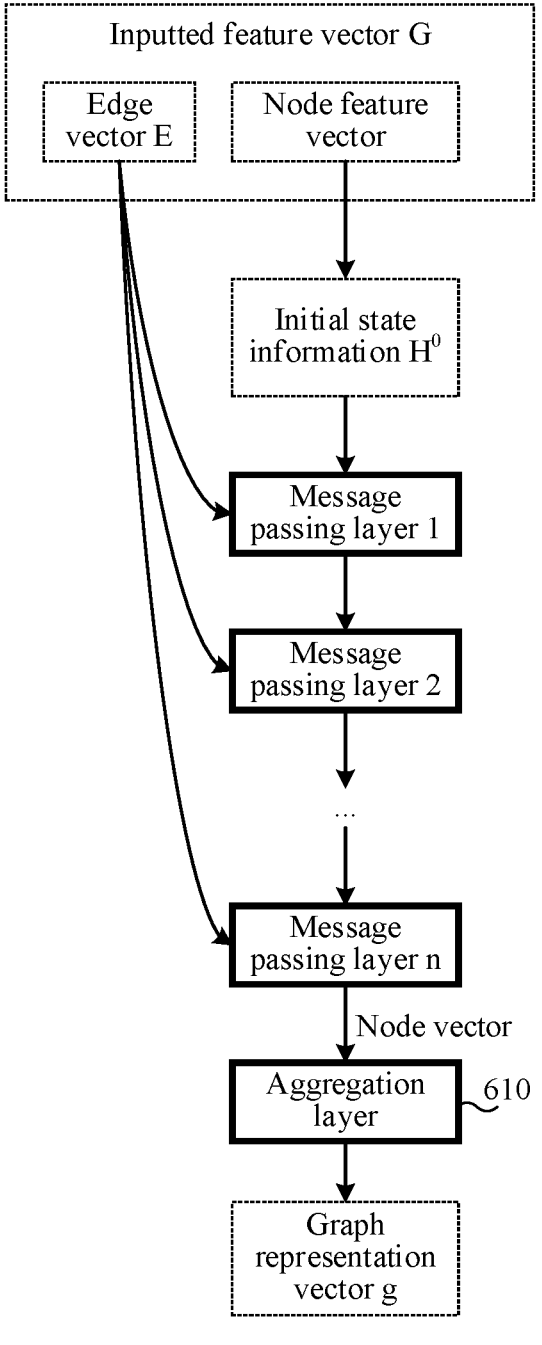
FIG. 6 is a schematic diagram of a network structure of an information propagation model according to an exemplary embodiment of this disclosure.

Based on the message passing layer shown in FIG. 5, a multi-layer node information propagation model based on edge sharing may be formed. FIG. 6 is a schematic diagram of a network structure of an information propagation model according to an exemplary embodiment of this disclosure.

As shown in FIG. 6, the model body is composed of a plurality of independent message passing layers, and an aggregation layer 610 is mainly responsible for converting an outputted node vector into a graph representation vector g with a fixed length, for example, in this embodiment of this disclosure, the conversion may be performed by using a sum function:

$$g = \sum_{v \in V} h_v$$

The graph representation vector g with a fixed length of any graph can be obtained by using the model shown in FIG. 6. The graph representation vector g with a fixed length may be used in a subsequent classification/regression model (that is, the classification model branch). For example, g may be inputted into a multi layer perceptron (MLP), and then a difference between the current model prediction and the actual label y is measured by using a cross entropy loss function. The calculation formula is as follows:

$$o_i = MLP(g_i)$$

$$loss(y_i, o_i) = CrossEntropy(y_i, o_i)$$

A model that can predict properties of different compounds can be obtained after training by using the foregoing model.

The final loss function may vary with specific tasks. For example, if the last task is a regression task, the loss function may be a mean squared error (MSE) loss function.

Based on the above, in the model training method provided by the embodiments of this disclosure, a feature vector sample is first processed by using a feature map extraction model branch to obtain a graph representation vector sample, the graph representation vector sample obtained based on a molecular structure of a compound sample is then processed by using a classification model branch to obtain a classification property of the compound sample, and finally parameters in the feature map extraction model branch and the classification model branch are adjusted according to an actual property of the compound sample and the classification property of the compound sample to obtain a compound analysis model with a training result converged that includes the feature map extraction model branch and the classification model branch. Therefore, the compound analysis model obtained through the training may obtain a graph representation vector that can accurately represent a feature of a compound based on a graph data structure of the compound, and can obtain a classification property of the compound based on the graph representation vector, thereby improving the accuracy of determining the classification property of the compound.

After the feature map extraction model branch and the classification model branch in the foregoing ML model are trained offline, the ML model can be applied to an analysis device to automatically classify the property of compound. For the application process, refer to the subsequent embodiments.

Figures 7, 8:
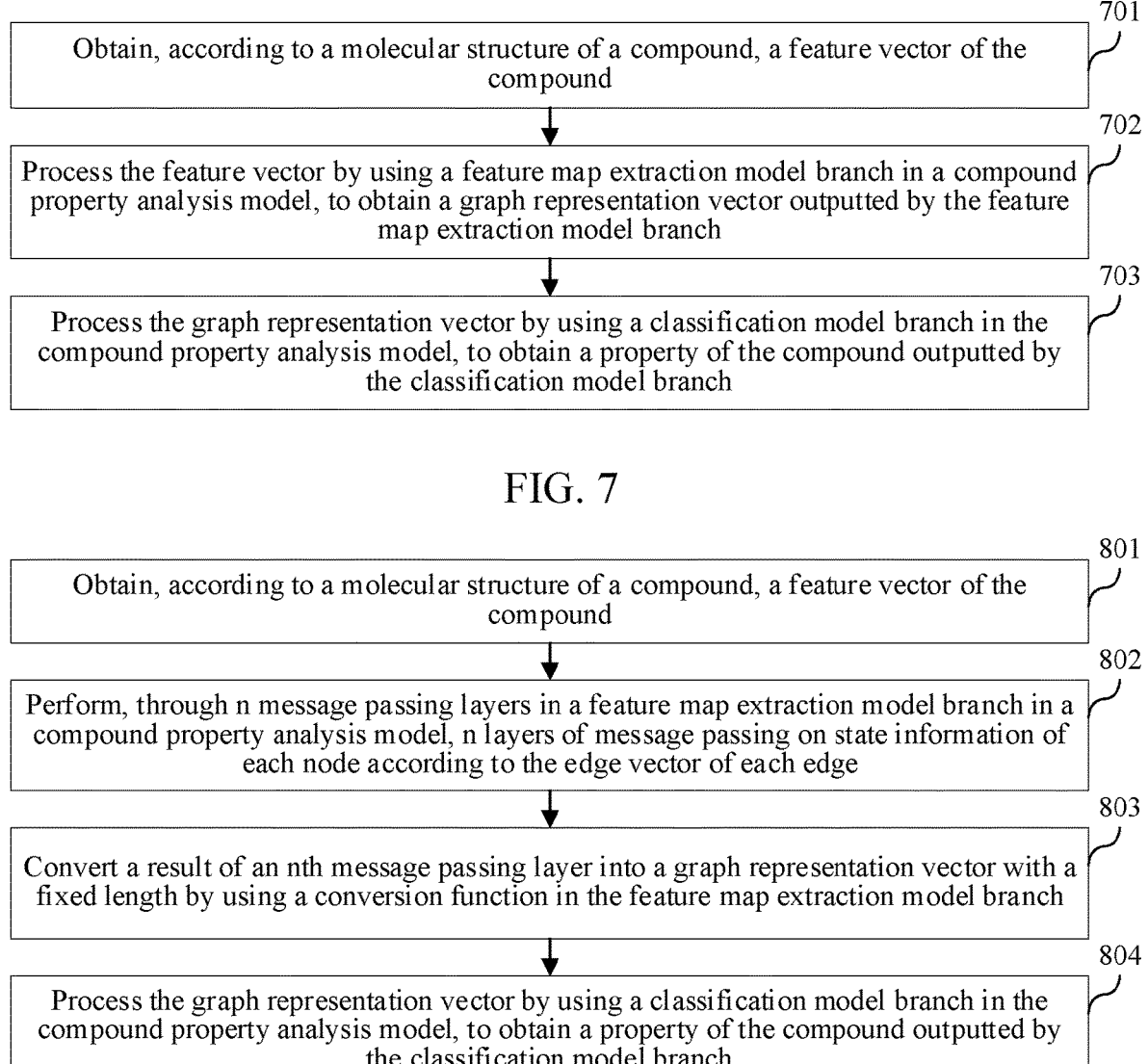
FIG. 7 is a flowchart of a compound property analysis method according to an exemplary embodiment of this disclosure.
FIG. 8 is a flowchart of a compound property analysis method according to an exemplary embodiment of this disclosure.

FIG. 7 is a flowchart of a compound property analysis method according to an exemplary embodiment of this disclosure. The compound property analysis method is performed by a computer device (processing circuitry). For example, the computer device may be the analysis device 120 shown in FIG. 1 to analyze and predict a property of a compound. As shown in FIG. 7, the compound property analysis method includes the following steps:

In Step 701, according to a molecular structure of a compound, a feature vector of the compound is obtained, the feature vector including a node vector of each node and an edge vector of each edge, the nodes being respectively corresponding to atoms in the molecular structure, and the edges being respectively corresponding to chemical bonds in the molecular structure.

In Step 702, the feature vector is processed by using a feature map extraction model branch in a compound property analysis model, to obtain a graph representation vector outputted by the feature map extraction model branch.

In Step 703, the graph representation vector is processed by using a classification model branch in the compound property analysis model, to obtain a property of the compound outputted by the classification model branch.

The compound property analysis model is an ML model trained according to a molecular structure of a compound sample and a property of the compound sample.

Based on the above, in the compound property analysis method shown in this embodiment, a feature vector of a compound is obtained according to a molecular structure of the compound; the feature vector is processed by using a feature map extraction model branch to obtain a graph representation vector; and the graph representation vector is processed by using a classification model branch to obtain a property of the compound. In this case, in the process of compound property analysis, the graph representation vector that can accurately represent a feature of the compound can be obtained based on a graph data structure of the compound, and a classification property of the compound can be obtained based on the graph representation vector, thereby improving the accuracy of determining the classification property of the compound.

FIG. 8 is a flowchart of a compound property analysis method according to an exemplary embodiment of this disclosure. The compound property analysis method is performed by a computer device (processing circuitry). For example, the computer device may be the analysis device 120 shown in FIG. 1 to analyze and predict a property of a compound. As shown in FIG. 8, the compound property analysis method includes the following steps:

In Step 801, according to a molecular structure of a compound, a feature vector of the compound is obtained, the feature vector including a node vector of each node and an edge vector of each edge, the nodes being respectively corresponding to atoms in the molecular structure, and the edges being respectively corresponding to chemical bonds in the molecular structure.

In this embodiment, when an analyst analyzes a molecular structure of a compound with an unknown property, the molecular structure of the compound may be inputted to a computer device for compound property analysis. For example, the computer device may be an analysis device storing the compound analysis model trained in the embodiment shown in FIG. 3.

For example, when the computer device is a terminal used by an analyst, the analyst may manually input or set the molecular structure of the compound in an input interface displayed on the terminal. Alternatively, when the computer device is a server that provides compound property analysis services externally, the analyst may log in to the server through the terminal, receive and display an input interface (for example, a web interface) provided by the server through the terminal, and manually input or set the molecular structure of the compound in the input interface, and the terminal transmits the molecular structure of the compound to the server.

After obtaining the molecular structure of the compound, the computer device obtains a feature vector of the compound according to the molecular structure of the compound, that is, in the form of a graph G(V,E).

For the definition and description of the feature vector, refer to the relevant content in the embodiment shown in FIG. 3. Details are not described herein again.

In Step 802, through n message passing layers in a feature map extraction model branch in a compound property analysis model, n layers of message passing are performed on state information of each node according to the edge vector of each edge, n being an integer greater than or equal to 2.

The compound property analysis model is an ML model trained according to a molecular structure of a compound sample and a property of the compound sample.

In one implementation, the compound property analysis model may be the ML model trained in the embodiment shown in FIG. 3.

In one implementation, the performing, through n message passing layers in a feature map extraction model branch, n layers of message passing on state information of each node according to the edge vector of each edge, n being an integer greater than or equal to 2 includes:

When a target message passing layer is a first layer in the n message passing layers, processing, through the target message passing layer, initial state information of each node according to the edge vector of each edge, to obtain state information corresponding to each node outputted from the first message passing layer, the target message passing layer being any one of the n message passing layers; and When a target message passing layer is a non-first layer in the n message passing layers, processing, through the target message passing layer, state information corresponding to each node outputted from a message passing layer previous to the target message passing layer according to the edge vector of each edge, to obtain state information corresponding to each node outputted from the target message passing layer.

For example, for an $i^{th}$ layer in the n message passing layers, (1) when i=1, through a first message passing layer in the feature map extraction model branch, initial state information of each node is processed according to the edge vector of each edge, to obtain state information corresponding to each node outputted from the first message passing layer; and (2) when $2 \leq i \leq n$, through an $i^{th}$ message passing layer in the feature map extraction model branch, state information corresponding to each node outputted from an $(i-1)^{th}$ message passing layer is processed according to the edge vector of each edge, to obtain state information corresponding to each node outputted from the $i^{th}$ message passing layer.

In one implementation, the message passing layer is configured to implement passing of message information and state information of each node by using a message aggregation function and a state fusion function; the state information of a first node at a moment t, the state information of a second node at the moment t, and an edge between the first node and the second node are processed by using the message aggregation function to obtain the message information of the first node at a moment t+1, the first node being any one of the nodes, and the second node being a neighbor node of the first node, t being a natural number; and the state information of the first node at the moment t and the message information of the first node at the moment t+1 are processed by using the state fusion function to obtain the state information of the first node at the moment t+1.

In Step 803, a result of an $n^{th}$ message passing layer is converted into a graph representation vector with a fixed length by using a conversion function in the feature map extraction model branch.

In one implementation, the conversion function in the step is a sum function, and the step is implemented as: processing the result of the $n^{th}$ message passing layer by using the sum function in the feature map extraction model branch, to obtain the graph representation vector with the fixed length.

In Step 804, the graph representation vector is processed by using a classification model branch in the compound property analysis model, to obtain a property of the compound outputted by the classification model branch.

The foregoing process of compound property analysis is similar to the process of model training in the embodiment shown in FIG. 3. The difference is that, in this embodiment, the model parameters are trained parameters and do not need to be updated through the loss function after the property of the compound is outputted.

Based on the above, in the compound property analysis method shown in this embodiment, a feature vector of a compound is obtained according to a molecular structure of the compound; the feature vector is processed by using a feature map extraction model branch to obtain a graph representation vector; and the graph representation vector is processed by using a classification model branch to obtain a property of the compound. In this case, in the process of compound property analysis, the graph representation vector that can accurately represent a feature of the compound can be obtained based on a graph data structure of the compound, and a classification property of the compound can be obtained based on the graph representation vector, thereby improving the accuracy of determining the classification property of the compound.

In addition, in the compound property analysis method shown in this embodiment, the state information and the message information of each node are passed by sharing the edge vectors between the nodes through a plurality of message passing layers. The state information of the node reflects the feature of each atom in the compound, and the edge vector reflects the feature of the chemical bond between the atoms. Therefore, the graph representation vector extracted in this solution can simultaneously reflect the features of the atom and the chemical bond in the compound, ensuring the accuracy of feature map extraction, and thereby improving the accuracy of subsequent compound property classification.

Figure 9:
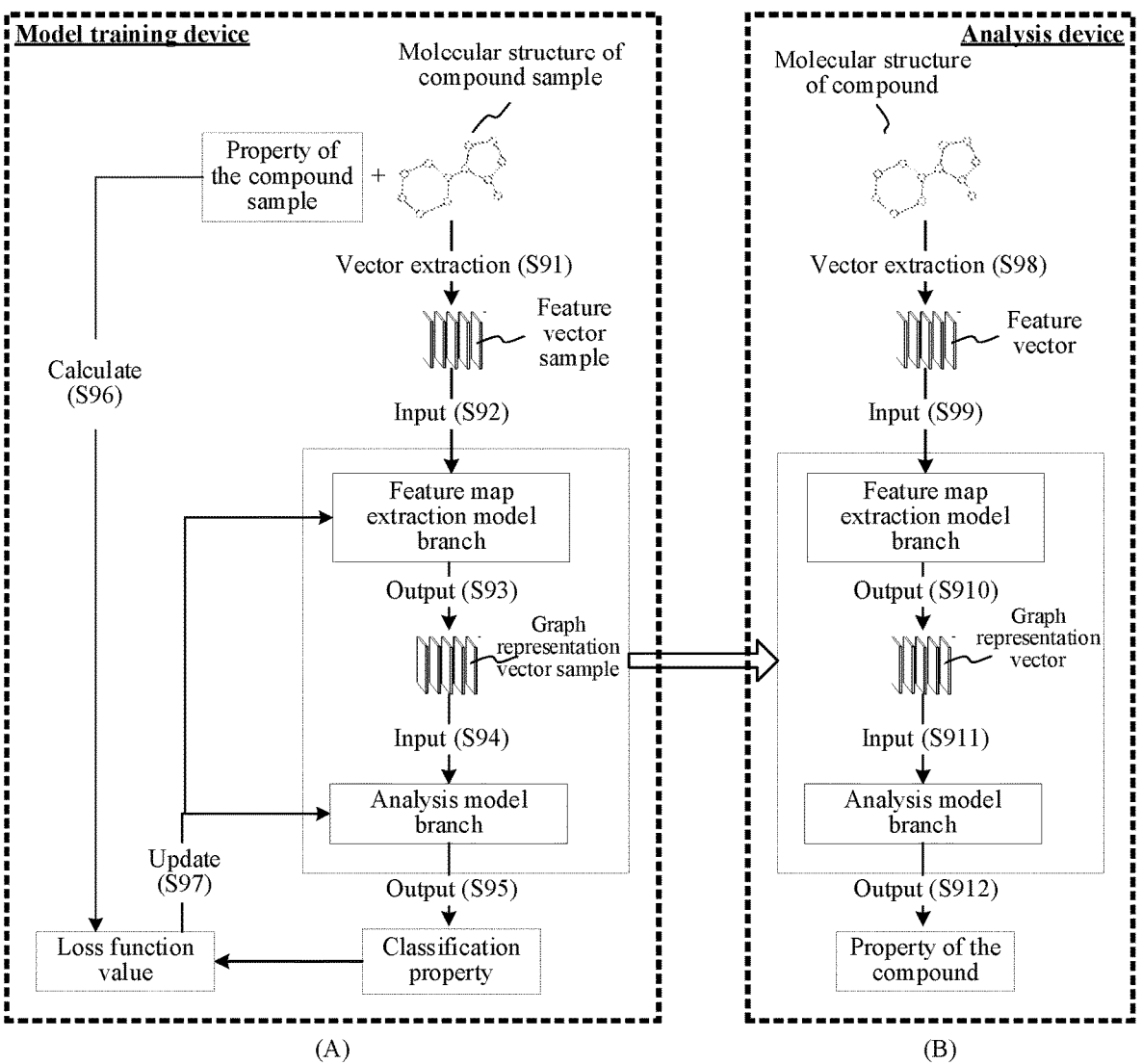
FIG. 9 is a schematic flowchart of training and application of a compound property analysis model according to an exemplary embodiment of this disclosure.

FIG. 9 is a schematic flowchart of training and application of a compound property analysis model according to an exemplary embodiment of this disclosure. As shown in FIG. 9, in a model training stage shown as part (A) in FIG. 9, after obtaining a molecular structure of a compound sample with a property marked, a model training device performs vector extraction on the molecular structure (S91), to obtain a feature vector sample, inputs the feature vector sample to a feature map extraction model branch in a compound property analysis model (S92), outputs a graph representation vector sample after processing the feature vector sample through a plurality of message passing layers in the feature map extraction model branch (S93), inputs the graph representation vector sample to a classification model branch in the compound property analysis model (S94), and outputs a classification property of the compound sample after processing the graph representation vector sample by using the classification model branch (S95). Then, the model training device calculates a loss function value according to the property of the compound sample and the classification property outputted by the model (S96), updates parameters in the feature map extraction model branch and the classification model branch according to the loss function value (S97) until the model training converges, and applies the trained compound property analysis model to an analysis device.

In a model application stage shown as part (B) in FIG. 9, after obtaining a molecular structure of a compound to be analyzed, the analysis device performs vector extraction on the molecular structure (S98), to obtain a feature vector, inputs the feature vector to the feature map extraction model branch in the compound property analysis model (S99), outputs a graph representation vector after processing the feature vector through a plurality of message passing layers in the feature map extraction model branch (S910), inputs the graph representation vector to the classification model branch in the compound property analysis model (S911), and outputs a property of the compound after processing the graph representation vector by using the classification model branch (S912).

The training and application solutions of the compound property analysis model shown in the embodiments of this disclosure may be applied to any AI analysis scenario involving properties of compounds and may be subsequently applied according to classified properties of compounds. For example, in the training and application solutions of the compound property analysis model shown in the embodiments of this disclosure, AI may perform preliminary property prediction on a compound with an unknown property, so that an analyst can perform further experimental analysis on the compound based on the property of the compound predicted by AI.

In the embodiments of this disclosure, the properties of the compound may be classified into various types of properties such as chemical properties, physical properties, and biological properties. To improve the accuracy of property analysis, different models may be used for different types of properties.

In one implementation, in the embodiments of this disclosure, before the feature vector is processed by using the feature map extraction model branch in the compound property analysis model to obtain the graph representation vector outputted by the feature map extraction model branch, the computer device may obtain a specified property type, and determine the corresponding compound property analysis model according to the property type.

For example, in the embodiment shown in FIG. 3, the model training device may separately train a compound property analysis model corresponding to each property type according to different types of properties of the compound sample. In this embodiment of this disclosure, when inputting a molecular structure of a compound to an analysis device, an analyst may select one or more property types to be analyzed on an interface provided by the analysis device, the analysis device determines a corresponding compound property analysis model according to the property type selected by the analyst and analyzes a property of the compound by using the corresponding compound property analysis model, and an analysis result may be fed back to the analyst through the interface.

Figures 10, 11:
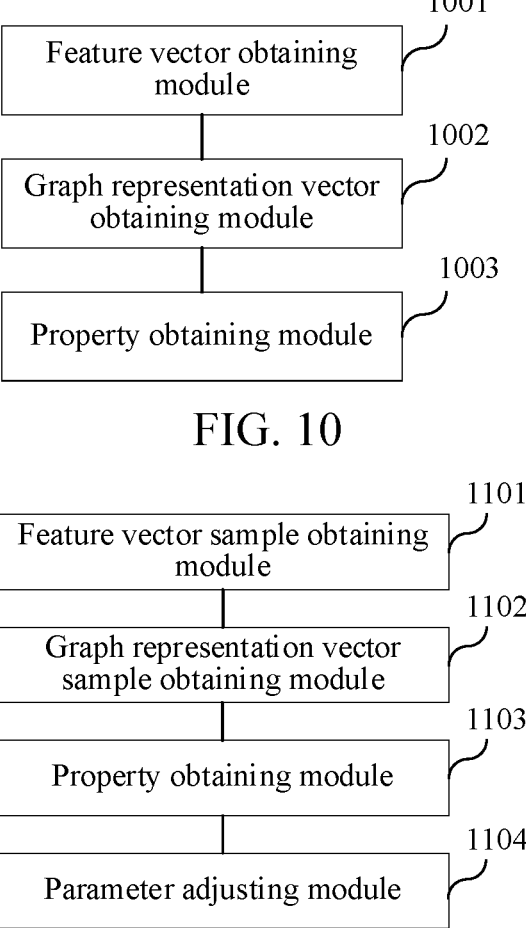
FIG. 10 is a structural block diagram of a compound property analysis apparatus according to an exemplary embodiment.
FIG. 11 is a structural block diagram of a model training apparatus according to an exemplary embodiment.

FIG. 10 is a structural block diagram of a compound property analysis apparatus according to an exemplary embodiment. The compound property analysis apparatus may be implemented by a computer device. For example, the computer device may be the analysis device 120 shown in FIG. 1 to perform all or some of the steps in the embodiment shown in FIG. 7 or FIG. 8. The compound property analysis apparatus may include a feature vector obtaining module 1001, a graph representation vector obtaining module 1002, and a property obtaining module 1003. One or more modules of the apparatus can be implemented by processing circuitry, software, or a combination thereof, for example.

The feature vector obtaining module 1001 is configured to obtain, according to a molecular structure of a compound, a feature vector of the compound, the feature vector including a node vector of each node and an edge vector of each edge, the nodes being respectively corresponding to atoms in the molecular structure, and the edges being respectively corresponding to chemical bonds in the molecular structure.

The graph representation vector obtaining module 1002 is configured to process the feature vector by using a feature map extraction model branch in a compound property analysis model, to obtain a graph representation vector outputted by the feature map extraction model branch.

The property obtaining module 1003 is configured to process the graph representation vector by using a classification model branch in the compound property analysis model, to obtain a property of the compound outputted by the classification model branch.

The term module (and other similar terms such as unit, submodule, etc.) in this disclosure may refer to a software module, a hardware module, or a combination thereof. A software module (e.g., computer program) may be developed using a computer programming language. A hardware module may be implemented using processing circuitry and/or memory. Each module can be implemented using one or more processors (or processors and memory). Likewise, a processor (or processors and memory) can be used to implement one or more modules. Moreover, each module can be part of an overall module that includes the functionalities of the module.

The compound property analysis model is an ML model trained according to a molecular structure of a compound sample and a property of the compound sample.

In one implementation, the graph representation vector obtaining module 902 includes: (1) a message passing sub-module, configured to perform, through n message passing layers in the feature map extraction model branch, n layers of message passing on state information of each node according to the edge vector of each edge, n being an integer greater than or equal to 2; and (2) a graph representation vector obtaining sub-module, configured to convert a result of an $n^{th}$ message passing layer into the graph representation vector with a fixed length by using a conversion function in the feature map extraction model branch.

In one implementation, the message passing sub-module is configured to, for an $i^{th}$ layer in the n message passing layers, (1) when i=1, process, through a first message passing layer in the feature map extraction model branch, initial state information of each node according to the edge vector of each edge, to obtain state information corresponding to each node outputted from the first message passing layer; and (2) when $2 \leq i \leq n$, process, through an $i^{th}$ message passing layer in the feature map extraction model branch, state information corresponding to each node outputted from an $(i-1)^{th}$ message passing layer according to the edge vector of each edge, to obtain state information corresponding to each node outputted from the $i^{th}$ message passing layer.

In one implementation, the message passing layer is configured to implement passing of message information and state information of each node by using a message aggregation function and a state fusion function; the message information of a first node at a moment t+1 is obtained by processing the state information of the first node at a moment t, the state information of a second node at the moment t, and an edge between the first node and the second node by using the message aggregation function; and the first node is any one of the nodes, and the second node is a neighbor node of the first node; and the state information of the first node at the moment t+1 is obtained by processing the state information of the first node at the moment t and the message information of the first node at the moment t+1 by using the state fusion function.

In one implementation, the graph representation vector obtaining sub-module is configured to process the result of the $n^{th}$ message passing layer by using a sum function in the feature map extraction model branch, to obtain the graph representation vector with the fixed length.

In one implementation, the apparatus further includes: (1) a property type obtaining module, configured to obtain a specified property type before the processing the feature vector by using a feature map extraction model branch in a compound property analysis model, to obtain a graph representation vector outputted by the feature map extraction model branch; and (2) an analysis model determining module, configured to determine the corresponding compound property analysis model according to the property type.

In one implementation, the property type includes at least one of a chemical property, a physical property, and a biological property.

Based on the above, in the compound property analysis method provided in this embodiment of this disclosure, a feature vector of a compound is obtained according to a molecular structure of the compound; the feature vector is processed by using a feature map extraction model branch to obtain a graph representation vector; and the graph representation vector is processed by using a classification model branch to obtain a property of the compound. In this case, in the process of compound property analysis, the graph representation vector that can accurately represent a feature of the compound can be obtained based on a graph data structure of the compound, and a classification property of the compound can be obtained based on the graph representation vector, thereby improving the accuracy of determining the classification property of the compound.

In addition, the compound property analysis apparatus shown in this embodiment of this disclosure is implemented on a computer device, and the state information and the message information of each node are passed by sharing the edge vectors between the nodes through a plurality of message passing layers. The state information of the node reflects the feature of each atom in the compound, and the edge vector reflects the feature of the chemical bond between the atoms. Therefore, the graph representation vector extracted in this solution can simultaneously reflect the features of the atom and the chemical bond in the compound, ensuring the accuracy of feature map extraction, and thereby improving the accuracy of subsequent compound property classification.

FIG. 11 is a structural block diagram of a model training apparatus according to an exemplary embodiment. The model training apparatus may be implemented on a computer device. For example, the computer device may be the model training device 110 shown in FIG. 1 to perform all or some of the steps in the embodiment shown in FIG. 3. The model training apparatus includes a feature vector sample obtaining module 1101, a graph representation vector sample obtaining module 1102, a property obtaining module 1103, and a parameter adjusting module 1104.

The feature vector sample obtaining module 1101 is configured to obtain, according to a molecular structure of a compound sample, a feature vector sample of the compound sample, the feature vector sample including a node vector of each node and an edge vector of each edge, the nodes being respectively corresponding to atoms in the molecular structure, and the edges being respectively corresponding to chemical bonds in the molecular structure.

The graph representation vector sample obtaining module 1102 is configured to process the feature vector sample by using a feature map extraction model branch in a compound property analysis model, to obtain a graph representation vector sample outputted by the feature map extraction model branch.

The property obtaining module 1103 is configured to process the graph representation vector sample by using a classification model branch in the compound property analysis model, to obtain a classification property of the compound sample outputted by the classification model branch.

The parameter adjusting module 1104 is configured to adjust parameters in the feature map extraction model branch and the classification model branch according to a property of the compound sample and the classification property of the compound sample.

In one implementation, the parameter adjusting module 1104 includes: (1) a loss function value obtaining sub-module, configured to input the property of the compound sample and the classification property of the compound sample to a loss function to obtain a loss function value; and (2) a parameter adjusting sub-module, configured to adjust the parameters in the feature map extraction model branch and the classification model branch according to the loss function value.

In one implementation, the parameter adjusting sub-module is configured to adjust, in response to the loss function value being greater than a preset threshold, the parameters in the feature map extraction model branch and the classification model branch according to the loss function value.

Based on the above, the model training apparatus shown in the embodiments of this disclosure is implemented on a computer device, a feature vector sample obtained based on a molecular structure of a compound sample is first processed by using a feature map extraction model branch to obtain a graph representation vector sample, the graph representation vector sample is then processed by using a classification model branch to obtain a classification property of the compound sample, and finally parameters in the feature map extraction model branch and the classification model branch are adjusted according to an actual property of the compound sample and the classification property of the compound sample to obtain a compound analysis model with a training result converged that includes the feature map extraction model branch and the classification model branch. Therefore, the compound analysis model obtained through the training may obtain a graph representation vector that can accurately represent a feature of a compound based on a graph data structure of the compound, and can obtain a classification property of the compound based on the graph representation vector, thereby improving the accuracy of determining the classification property of the compound.

Figure 12:
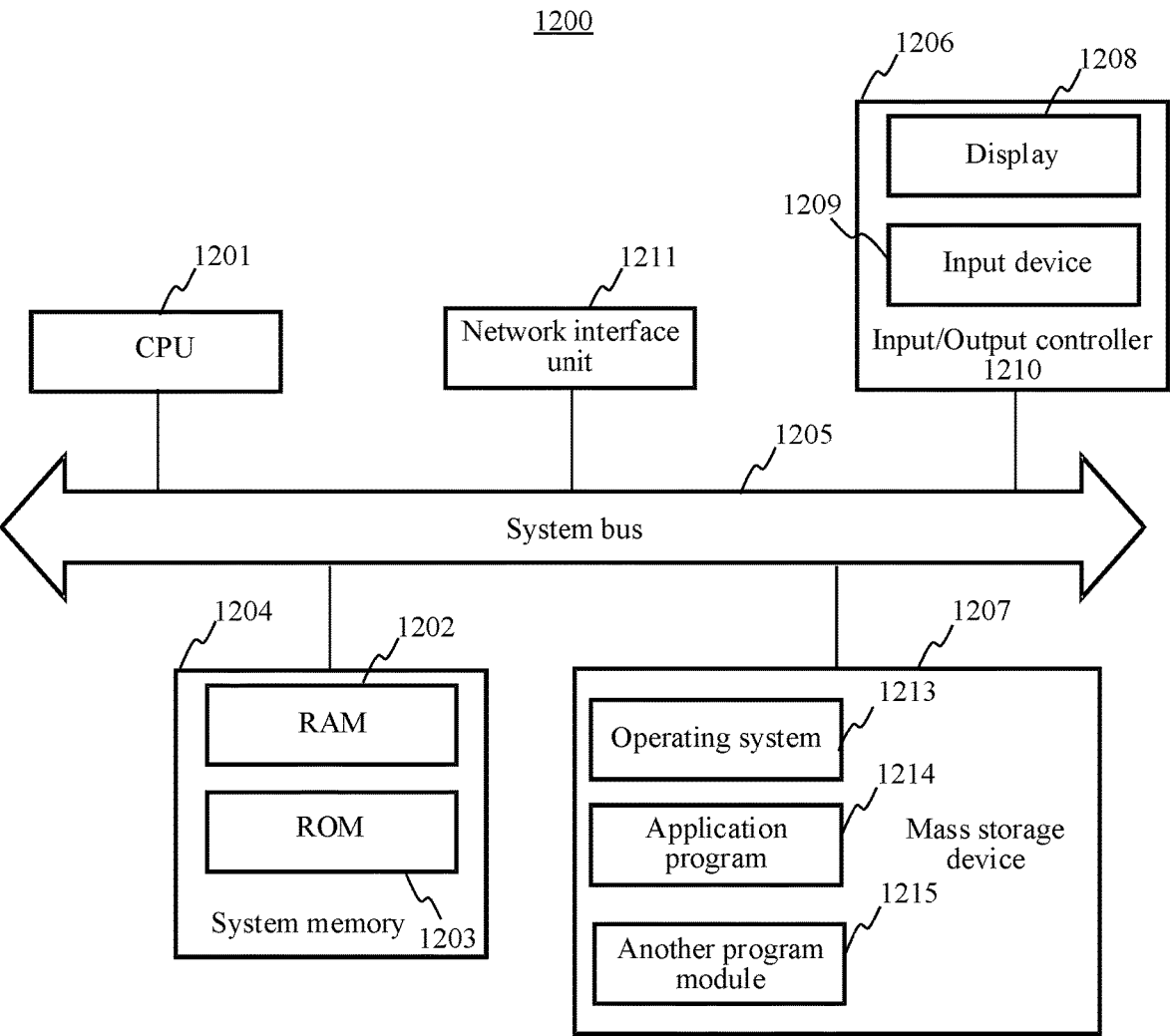
FIG. 12 is a schematic structural diagram of a computer device according to an exemplary embodiment.

FIG. 12 is a schematic structural diagram of a computer device according to an exemplary embodiment. The computer device may be the model training device 110 and the analysis device 120 shown in FIG. 1. The computer device 1200 includes a central processing unit (CPU) 1201, a system memory 1204 including a random access memory (RAM) 1202 and a read-only memory (ROM) 1203, and a system bus 1205 connecting the system memory 1204 to the CPU 1201. The computer device 1200 further includes a basic input/output (I/O) system 1206 assisting in transmitting information between components in a computer, and a mass storage device 1207 configured to store an operating system 1213, an application program 1214, and another program module 1215.

The basic I/O system 1206 includes a display 1208 configured to display information and an input device 1209 such as a mouse or a keyboard that is configured for information inputting by a user. The display 1208 and the input device 1209 are both connected to the CPU 1201 by an input and output controller 1210 connected to the system bus 1205. The basic I/O system 1206 may further include the input and output controller 1210, to receive and process inputs from a plurality of other devices, such as the keyboard, the mouse, or an electronic stylus. Similarly, the input and output controller 1210 further provides an output to a display screen, a printer, or another type of output device.

The mass storage device 1207 is connected to the CPU 1201 by using a mass storage controller (not shown) connected to the system bus 1205. The mass storage device 1207 and an associated non-transitory computer-readable medium provide non-volatile storage for the computer device 1200. That is, the mass storage device 1207 may include a computer-readable medium (not shown) such as a hard disk or a compact disc read only memory (CD-ROM) drive.

In general, the computer-readable medium may include a computer storage medium and a communication medium. The computer-storage medium includes volatile and non-volatile media, and removable and non-removable media implemented by using any method or technology used for storing information such as computer-readable instructions, data structures, program modules, or other data. The computer storage medium includes a RAM, a ROM, an erasable programmable ROM (EPROM), an electrically erasable programmable ROM (EEPROM), a flash memory or another solid-state memory technology, a CD-ROM, a digital versatile disc (DVD) or another optical memory, a magnetic cassette, a magnetic tape, a magnetic disk memory, or another magnetic storage device. Certainly, a person skilled in the art may learn that the computer storage medium is not limited to the foregoing several types. The system memory 1204 and the mass storage device 1207 may be collectively referred to as a memory.

The computer device 1200 may be connected to the Internet or another network device by using a network interface unit 1211 connected to the system bus 1205.

The memory further includes one or more programs. The one or more programs are stored in the memory. The CPU 1201, an example of processing circuitry, executes the one or more programs to implement all or some steps of the method shown in FIG. 3, FIG. 7, or FIG. 8.

Figure 13:
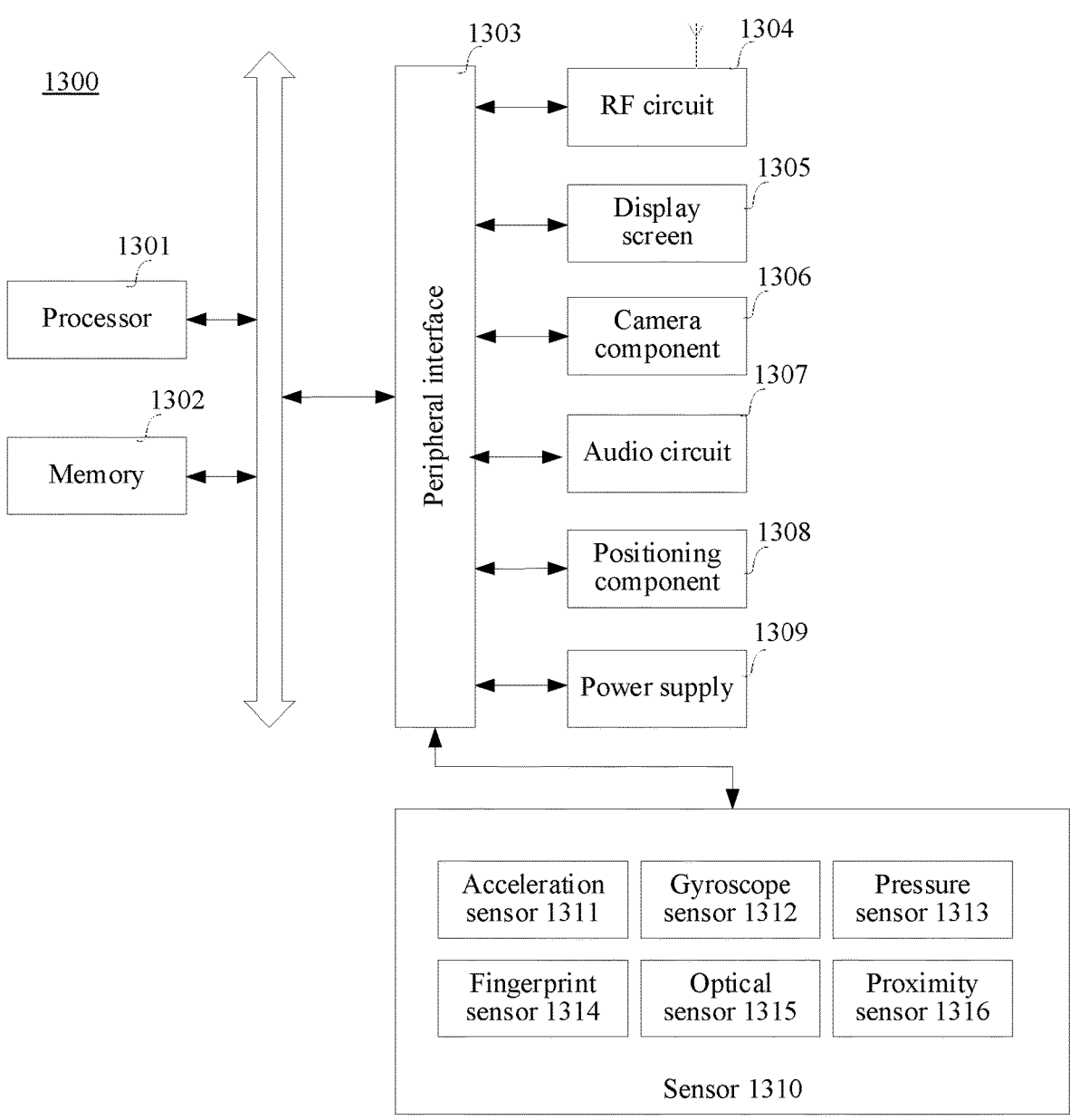
FIG. 13 is a structural block diagram of a computer device according to an exemplary embodiment.

FIG. 13 is a structural block diagram of a computer device 1300 according to an exemplary embodiment. The computer device 1300 may be the analysis device 120 shown in FIG. 1.

Generally, the computer device 1300 includes a processor 1301 and a memory 1302.

The processor 1301 may include one or more processing cores, for example, a 4-core processor or an 8-core processor. The processor 1301 may be implemented in at least one hardware form of digital signal processor (DSP), a field-programmable gate array (FPGA), and a programmable logic array (PLA). The processor 1301 may also include a main processor and a coprocessor. The main processor is a processor configured to process data in an awake state, and is also referred to as a CPU. The coprocessor is a low power consumption processor configured to process data in a standby state. In some embodiments, the processor 1301 may be integrated with a graphics processing unit (GPU). The GPU is configured to be responsible for rendering and drawing content that a display needs to display. In some embodiments, the processor 1301 may further include an AI processor. The AI processor is configured to process a computing operation related to ML.

The memory 1302 may include one or more computer-readable storage media that may be non-transitory. The memory 1302 may further include a high-speed RAM, and a non-volatile memory such as one or more magnetic disk storage devices and a flash storage device. In some embodiments, the non-transitory computer-readable storage medium in the memory 1302 is configured to store at least one instruction, and the at least one instruction is configured to be executed by the processor 1301 to implement the method performed by an analysis device provided in the method embodiments of this disclosure.

In some embodiments, the computer device 1300 further includes a peripheral interface 1303 and at least one peripheral. The processor 1301, the memory 1302, and the peripheral interface 1303 may be connected through a bus or a signal cable. Each peripheral may be connected to the peripheral interface 1303 through a bus, a signal cable, or a circuit board. Specifically, the peripheral includes at least one of a radio frequency (RF) circuit 1304, a display screen 1305, a camera component 1306, an audio circuit 1307, a positioning component 1308, and a power supply 1309.

In some embodiments, the computer device 1300 further includes one or more sensors 1310. The one or more sensors 1310 include, but are not limited to, an acceleration sensor 1311, a gyroscope sensor 1312, a pressure sensor 1313, a fingerprint sensor 1314, an optical sensor 1315, and a proximity sensor 1316.

A person skilled in the art may understand that the structure shown in FIG. 13 does not constitute any limitation on the computer device 1300, and the computer device may include more components or fewer components than those shown in the figure, or some components may be combined, or a different component deployment may be used.

In an exemplary embodiment, a non-transitory computer-readable storage medium including an instruction is further provided, for example, a memory including at least one instruction, at least one program, a code set, or an instruction set. The at least one instruction, the at least one program, the code set, or the instruction set may be executed by a processor to implement all or some steps of the method shown in any embodiment in FIG. 3, FIG. 7, or FIG. 8. For example, the non-transitory computer-readable storage medium may be a ROM, a RAM, a CD-ROM, a magnetic tape, a floppy disk, and an optical data storage device.

In an exemplary embodiment, a computer program product or a computer program is provided. The computer program product or the computer program includes computer instructions, and the computer instructions are stored in a computer-readable storage medium. A processor of a computer device reads the computer instructions from the computer-readable storage medium, and executes the computer instructions, to cause the computer device to perform all or some steps of the method shown in any embodiment in FIG. 3, FIG. 7, or FIG. 8.

Other embodiments of this disclosure will be understood to a person skilled in the art from consideration of the specification and practice of the disclosure here. This disclosure is intended to cover any variations, uses or adaptive changes of this disclosure. Such variations, uses or adaptive changes follow the general principles of this disclosure. The specification and the embodiments are considered as merely exemplary, and the scope and spirit of this disclosure are pointed out in the following claims.

It is to be understood that this disclosure is not limited to the precise structures described above and shown in the accompanying drawings, and various modifications and changes can be made without departing from the scope of this disclosure. The scope of this disclosure is subject only to the appended claims.

What is claimed is:

1. A compound property analysis method performed by a computer device, the method comprising:
    obtaining, according to a molecular structure of a compound, a feature vector of the compound, the feature vector comprising a node vector of each node and an edge vector of each edge, the nodes respectively corresponding to atoms in the molecular structure, and the edges respectively corresponding to chemical bonds in the molecular structure;
    processing the feature vector, by using the computer device through a compound property analysis model that includes a feature map extraction model branch configured to perform message passing across a plurality of layers, to generate a graph representation vector; and
    processing the graph representation vector by using a classification model branch in the compound property analysis model, the classification model branch being configured to determine a predicted property type of the compound based on the graph representation vector,
    the compound property analysis model being a machine learning (ML) model trained according to a molecular structure of a compound sample and a corresponding property type of the compound sample.

2. The method according to claim 1, wherein the processing the feature vector further comprises:
    performing, through n message passing layers in the feature map extraction model branch, n layers of message passing on state information of each node according to the edge vector of each edge, n being an integer greater than or equal to 2; and
    converting a result of an $n^{th}$ message passing layer into the graph representation vector with a fixed length by using a conversion function in the feature map extraction model branch.

3. The method according to claim 2, wherein the performing further comprises:
    for an $i^{th}$ layer in the n message passing layers,
        when i=1, processing, through a first message passing layer in the feature map extraction model branch, initial state information of each node according to the edge vector of each edge, to obtain the state information corresponding to each node outputted from the first message passing layer; and
        when $2 \leq i \leq n$, processing, through an $i^{th}$ message passing layer in the feature map extraction model branch, the state information corresponding to each node outputted from an $(i-1)^{th}$ message passing layer according to the edge vector of each edge, to obtain state information corresponding to each node outputted from the $i^{th}$ message passing layer.

4. The method according to claim 3, wherein a message passing layer of the plurality of layers is configured to perform message aggregation and state fusion, comprising:
    obtaining message information of a first node at a moment t+1 by processing the state information of the first node at a moment t, the state information of a second node at the moment t, and an edge between the first node and the second node by using a message aggregation function; and
    obtaining state information of the first node at the moment t+1 by processing the state information of the first node at the moment t and the message information of the first node at the moment t+1 by using a state fusion function.

5. The method according to claim 2, wherein the converting further comprises:
    processing the result of the $n^{th}$ message passing layer by using a sum function in the feature map extraction model branch, to obtain the graph representation vector with the fixed length.

6. The method according to claim 1, wherein before the processing the feature vector by using the feature map extraction model branch, the method further comprises:
    obtaining the property type corresponding to the compound; and
    selecting the corresponding compound property analysis model according to the property type.

7. The method according to claim 6, wherein the property type comprises at least one of a chemical property, a physical property, and a biological property.

8. A model training method performed by a computer device, the method comprising:

obtaining, according to a molecular structure of a compound sample, a feature vector sample of the compound sample, the feature vector sample comprising a node vector of each node and an edge vector of each edge, the nodes respectively corresponding to atoms in the molecular structure, and the edges respectively corresponding to chemical bonds in the molecular structure;

processing the feature vector sample by using the computer device through a compound property analysis model that includes a feature map extraction model branch configured to perform message passing across a plurality of layers, to generate a graph representation vector sample;

processing the graph representation vector sample by using a classification model branch in the compound property analysis model, the classification model branch being configured to determine a predicted property type of the compound sample based on the graph representation vector sample; and adjusting parameters in the feature map extraction model branch and the classification model branch according to a property of the compound sample and the predicted property type.

9. The method according to claim 8, wherein the adjusting parameters further comprises:

inputting the property type of the compound sample and the classification predicted property type to a loss function to obtain a loss function value; and adjusting the parameters in the feature map extraction model branch and the classification model branch according to the loss function value.

10. The method according to claim 9, wherein the adjusting the parameters in the feature map extraction model branch and the classification model branch according to the loss function value further comprises:

adjusting, in response to the loss function value being greater than a preset threshold, the parameters in the feature map extraction model branch and the classification model branch according to the loss function value.

11. A compound property analysis apparatus, the apparatus comprising:

circuitry configured to obtain, according to a molecular structure of a compound, a feature vector of the compound, the feature vector comprising a node vector of each node and an edge vector of each edge, the nodes respectively corresponding to atoms in the molecular structure, and the edges respectively corresponding to chemical bonds in the molecular structure;

process the feature vector, by using a compound property analysis model that includes a feature map extraction model branch configured to perform message passing across a plurality of layers, to generate a graph representation vector; and process the graph representation vector by using a classification model branch in the compound property analysis model, the classification model branch being configured to determine a predicted property type of the compound based on the graph representation vector, the compound property analysis model being a machine learning (ML) model trained according to a molecular structure of a compound sample and a corresponding property type of the compound sample.

12. The apparatus according to claim 11, wherein the circuitry is further configured to:

perform, through n message passing layers in the feature map extraction model branch, n layers of message passing on state information of each node according to the edge vector of each edge, n being an integer greater than or equal to 2; and convert a result of an $n^{th}$ message passing layer into the graph representation vector with a fixed length by using a conversion function in the feature map extraction model branch.

13. The apparatus according to claim 12, wherein the circuitry is further configured to, for an $i^{th}$ layer in the n message passing layers, when i=1, process, through a first message passing layer in the feature map extraction model branch, initial state information of each node according to the edge vector of each edge, to obtain the state information corresponding to each node outputted from the first message passing layer; and when 2≤i≤n, process, through an $i^{th}$ message passing layer in the feature map extraction model branch, state information corresponding to each node outputted from an $(i-1)^{th}$ message passing layer according to the edge vector of each edge, to obtain the state information corresponding to each node outputted from the $i^{th}$ message passing layer.

14. The apparatus according to claim 12, wherein a message passing layer of the plurality of layers is configured to perform message aggregation and state fusion, comprising:

obtaining message information of a first node at a moment t+1 by processing the state information of the first node at a moment t, the state information of a second node at the moment t, and an edge between the first node and the second node by using a message aggregation function; and obtaining state information of the first node at the moment t+1 by processing the state information of the first node at the moment t and the message information of the first node at the moment t+1 using a state fusion function.

15. The apparatus according to claim 12, wherein the circuitry is further configured to process the result of the $n^{th}$ message passing layer by using a sum function in the feature map extraction model branch, to obtain the graph representation vector with the fixed length.

16. The apparatus according to claim 11, wherein the circuitry is further configured to:

obtain the property type corresponding to the compound; and select the corresponding compound property analysis model according to the property type.

17. The apparatus according to claim 16, wherein the property type obtained by the circuitry comprises at least one of a chemical property, a physical property, and a biological property.

18. A computer device, comprising processing circuitry and a memory, the memory storing at least one instruction, at least one program, a code set, or an instruction set, the at least one instruction, the at least one program, the code set, or the instruction set being loaded and executed by the processing circuitry to implement the compound property analysis method according to claim 1.

19. A non-transitory computer-readable storage medium, the storage medium storing at least one instruction, at least one program, a code set, or an instruction set, the at least one instruction, the at least one program, the code set, or the instruction set being loaded and executed by processing circuitry to implement the compound property analysis method according to claim 1.

20. A non-transitory computer-readable storage medium, the storage medium storing at least one instruction, at least one program, a code set, or an instruction set, the at least one instruction, the at least one program, the code set, or the instruction set being loaded and executed by processing circuitry to implement the compound property analysis method according to claim 8.

* * * * *